United States Patent
Penelle et al.

(10) Patent No.: US 6,486,344 B1
(45) Date of Patent: Nov. 26, 2002

(54) POLYMER COATINGS WITH IMPROVED ADHESION PROPERTIES ON METALLIC SURFACES

(76) Inventors: Jaques Penelle, 81 Mount Warner Rd., Hadley, MA (US) 01035; Tao Xie, G009 N. Village, Amherst, MA (US) 01002; Kanad Das, 950 N. Pleasant St. #71, Amherst, MA (US) 01002

( * ) Notice: Subject to any disclaimer, the term of this patent is extended or adjusted under 35 U.S.C. 154(b) by 0 days.

(21) Appl. No.: 09/915,718

(22) Filed: Jul. 26, 2001

(51) Int. Cl.$^7$ .............. C07C 229/00; C07C 233/00; C07C 235/00; C07C 237/00; C07C 239/00
(52) U.S. Cl. ..................... 560/172; 564/199
(58) Field of Search ............. 560/172; 564/199

(56) References Cited

U.S. PATENT DOCUMENTS

| | | | |
|---|---|---|---|
| 4,613,658 A | * 9/1986 | Mathias et al. | 526/312 |
| 4,906,767 A | * 3/1990 | Mathias et al. | 560/13 |
| 5,871,755 A | * 2/1999 | Genard et al. | 424/401 |

FOREIGN PATENT DOCUMENTS

| | | |
|---|---|---|
| GB | 1354571 | * 5/1974 |

OTHER PUBLICATIONS

"The preparation of poly(N–acetyl–alpha–amino acrylic acid)[poly(N–acetyl dehydroalanine] and Poly(alpha–amino acrylic acid)(polydehydroalanine)" Asquith et al, J. Pol. Sci. vol. 16 pp3275–3280 (1978).*

* cited by examiner

Primary Examiner—Mukund J. Shah
Assistant Examiner—Zachary C. Tucker
(74) Attorney, Agent, or Firm—William B. Ritchie

(57) ABSTRACT

The present invention is based on a series of acrylic cross-linking agents containing two or more dehydroalanine moieties ($H_2C$=$C(NHCOR')COOR$) per monomer. Monomers of the general structure $H_2C$=$C(NHCOCH_3)COO(CH_2)_iOO(CH_3CONH)C$=$CH_2$ with i=4, 5, and 8 can be polymerized or copolymerized under UV-curing conditions or by simple heating above melting point, leading to cross-linked polymeric materials. When polymerized on metallic surfaces, exceptional adhesion is obtained with no need for additional adhesion enhancers.

1 Claim, No Drawings

POLYMER COATINGS WITH IMPROVED ADHESION PROPERTIES ON METALLIC SURFACES

FIELD OF THE INVENTION

This invention relates to the field of polymer coatings and, in particular, to acrylic cross-linking agents.

BACKGROUND OF THE INVENTION

Polymer coatings are used commercially in a variety of applications. These include cross-linked resins for electronic and imaging industries, dental materials and other biomaterials, and hot melt adhesives. Additionally, polymeric layers are used for sensors containing a metallic interface such as quartz crystal microbalance (QCM). Polymer coatings are thus used on a wide range of substrates (metals, plastics, wood, body parts, etc.).

Polymer coatings on these various substrates are generally obtained by curing formulations containing polymerizable monomers. Many different technologies well known in the art can be used to cure the formulation, such as UV light, electron beam, radiation, or thermal curing. When free radicals are generated in the process, acrylic monomers are preferably used and account for the vast majority of commercial applications currently in use.

Use of acrylic monomers poses several well-known problems, including poor adhesion on metallic surface (in particular noble metals) and possible health/ environmental damage caused by the unreacted monomer. The problem of poor adhesion to metallic surfaces has a long history in polymer science and engineering and is considered one of the key issues in polymer curing on metallic surfaces. The physics of the phenomenon may be complex in its details, but the rationale for the poor adhesion is well known and understood: the polymer film shrinks during the curing while the underlying metallic substrate does not. This generates a large amount of stress at the interface. The problem is particularly difficult to solve for surfaces made of noble metals due to lack of chemical interactions at the interface between the metal and polymer coating. Most strategies to overcome the problem rely on well-known modifications of the metallic surface, such as metal surface oxidation or deposition of so-called "primers".

Therefore, what is needed is a polymer coating that allows for superior adhesion to metallic surfaces, particularly to the noble metals. Also, a coating is needed that is less harmful to the environment and is less toxic than coatings made from traditional acrylic monomers.

SUMMARY OF THE INVENTION

The present invention is a polymer coating with superior adhesion properties. The invention is based on the development of a new series of acrylic cross-linking agents containing two or more dehydroalanine moieties ($H_2C=C(NHCOR')COOR$) per monomer instead of the traditional acrylic ($H_2C=CHCOOR$) or methacrylic ($H_2C=C(CH_3)COOR$) moieties. These vinyl monomers are not found in the prior art with the exception of a urea-containing system disclosed in U.S. Pat. Nos. 4,906,767 and 4,985,522 issued to Mathias et al, which discloses similar units, but does not disclose the structure of the present invention. Based on the properties disclosed in the prior art, it is doubtful those structures could be used as polymer coatings with suitable adhesion properties.

Monomers of the general structure $H_2C=C(NHCOCH_3)COO(CH_2)_iOO(CH_3 CONH)C=CH_2$ with i=4, 5, or 8 can be polymerized or copolymerized under UV-curing conditions or by simple heating above melting point, leading to cross-linked polymeric materials. Spontaneous and rapid thermal polymerization points to a new family of hot melt adhesives with tunable reactivities and high shelf-life stabilities below their melting point. When polymerized on metallic surfaces, exceptional adhesion is obtained with no need for additional adhesion enhancers.

Therefore, it is an aspect of this invention to provide a new series of acrylic cross-linking agents for use in forming polymer coatings.

It is another aspect of the invention to use novel acrylic monomers to allow superior adhesion to metallic surfaces.

It is a further aspect of this invention to provide a polymer coating with exceptional adhesion properties without the use of additional adhesion enhancers.

It is a further aspect of the invention to provide a polymer coating that may be less toxic than coatings formed from traditional acrylic monomers.

It is a further aspect of the invention to provide a coating formed by spontaneous and rapid thermal polymerization.

These aspects of the invention are not mean to be exclusive and other features, aspects, and advantages of the present invention will be readily apparent to those of ordinary skill in the art when read in conjunction with the appended claims.

DETAILED DESCRIPTION OF THE INVENTION

The present invention is the result of experimenting with on-chip polymerization of molecular imprinting agents to provide MIP-functionalized QCM probes. Several approaches were explored for the synthesis of heavily cross-linked acrylic networks on the gold-made surface of a QCM probe.

The on-chip cross-linked coatings synthesized and studied for this invention were all obtained by fast UV-photopolymerization of a thin liquid film containing a commercial bis- or trisacrylate (tripropyleneglycol diacrylate (TPGDA) or trimethylopropane triacrylate (TMPTA)), a reactive diluent (benzyl methacrylate), a photoinitiator (2-benzyl-2-dimethylamino-4'-morpholino-butyrophenone (Irgacure 369), azo-bis(isobutyronitrile) (AIBN) or tetraethylthiuram disulfide (TETD)) and various additives aimed at improving the adhesion of the final cross-linked polymer on the gold surface. The initial thin liquid film was obtained by spin coating a few microliters of a solution containing the reagents diluted in tetrahydrofuran (THF) or dichloromethane. The film had previously been deposited on the gold surface of the chip. The light source used in these experiments has a very high intensity allowing most of the photopolymerization to occur in less than 20 seconds. The exact amounts of each monomer/reagent and detailed experimental conditions are provided below.

Preliminary experiments with 'simple' acrylic networks obtained by photoirradiation of TPGDA and benzyl methacrylate indicated a limited adhesion of the film on the metallic surface: the film peeled off after immersion in either dichloromethane or acetonitrile. This behavior was both expected and surprising. It was surprising because claims made in the recent literature imply that conditions can be found to obtain good adhesion of acrylic or styrenic polymers on a gold surface. It was expected as this problem has a long history in polymer science and engineering and is still considered today as one of the key problem in UV-curing on metallic surfaces (UV-cured paintings or plastic coatings on cars are traditional examples). The physics of the phenomenon is complex in its details, but the rationale for the poor adhesion is well known and understood: the polymer film shrinks during the curing while the underlying metallic substrate does not, generating a very large amount of stress at the interface.

Strategies that were successively considered to solve this problem include:
1. use of acrylic acid as a co-monomer,
2. use of itaconic acid as a co-monomer,
3. modification of the gold surface with a thiol-capped acrylic monomer able to self-assemble on the surface,
4. use of tetraethylthiuram disulfide as a photoinitiator or chain-transfer agent,
5. use of triacrylate (TMPTA) as the multifunctional monomer,
6. use of bis(dehydroalanine) (DBHA) as the multifunctional monomer.

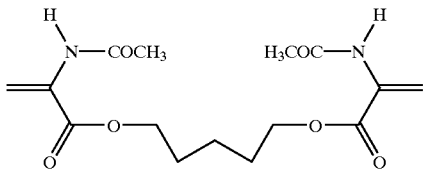

Figure 1. Bis(dehydroalanine).

The rationale for the above curing conditions is as follows:
(1 and 2). Introduce carboxylic acid for improved adhesion with the gold surface. This strategy has been recently used in a MIP experiment (Haupt, K.; Noworyta, K.; Kuter, W. *Anal Commun.*, 1999, 36, 391–393).
(3 and 4). Introduction of sulfur-containing groups for improved adhesion with the gold surface.
(5). Different stress buildup in the film.
(6). Monomer was available and had been shown to improve adhesion on several substrates.

None of the coatings obtained using strategies 1–5 showed adequate adhesion, although not enough conditions have been investigated experimentally to disprove the possibility that under slightly different conditions they might work. The use of the monomer shown in FIG. 1 solved the adhesion problem, however, and no further experiments to test the other strategies have been tested.

Experiments have demonstrated that monomers of the general structure $H_2C=C(NHCOCH_3)COO(CH_2)_iOO(CH_3CONH)C=CH_2$ with i=4, 5, or 8 can be polymerized or copolymerized under UV-curing conditions or by simple heating above melting point, leading to cross-linked polymeric materials. When (co)polymerized on the surface of gold, exceptional adhesion is obtained with no need for additional adhesion enhancers. Following is a general synthetic procedure used to obtain these monomers.

General synthetic procedure for α,ω-alkanediol bis(α-acetamido acrylate)s: A mixture of α-acetamidoacrylic acid (0,016 mol, 2.064 g), α,ω-alkanedibromide(0.06 mol), $K_2CO_3$ (1.8 g) and DMSO (20 mL was stirred at room temperature for four days. 30 mL of doionized water was introduced and the resulting mixture was extracted with chloroform (30 mL×2). The chloroform phases were collected and washed with water (15 mL×3). The chloroform phase was dried over magnesium sulfate. Chloroform was evaporated by rotavapor and a solid was obtained. The remaining solvent was further removed under vacuum at room temperature to give a white solid product.

The following examples present the percent product (yield) obtained after reaction, as well as the theoretical and actual percent mass of C, H, and N.

EXAMPLES (1) i=4.

1,4-butanediol bis(α-acetamido acrylate) Yield: 85%; $^1$H NMR (CDCl$_3$, 300 MHz): δ (ppm)=1.76 (m, 4H, CO$_2$CH$_2$C$\underline{H}_2$), 2.05 (s, 6H, CH$_3$), 4.20 (t, 4H, CO$_2$C$\underline{H}_2$CH$_2$), 5.78 (s, 2H, vinyl C$\underline{H}$), 6.52 (s, 2H, vinyl C$\underline{H}$). 7.63 (s, 2H, N$\underline{H}$)

| $C_{14}H_{20}O_6N_2$ (312.3) | Calc | C 53.84 | H 6.45 | N 8.97 |
|---|---|---|---|---|
| | Found | C 53.60 | H 6.65 | N 8.43 |

(2) i=5

1,5-pentanediol bis(α-acetamido acrylate) Yield: 61%; $^1$H NMR (CDCl$_3$, 300 MHz): δ (ppm)=1.43 (p, 2H, CO$_2$CH$_2$CH$_2$C$\underline{H}_2$), 1.72 (p, 4H, CO$_2$CH$_2$C$\underline{H}_2$), 2.06 (s, 6H, CH$_3$), 4.20 (t, 4H, CO$_2$C$\underline{H}_2$CH$_2$), 5.79 (s, 2H, vinyl C$\underline{H}$), 6.53 (s, 2H, vinyl C$\underline{H}$), 7.68 (s, 2H, N$\underline{H}$)

| $C_{15}H_{22}O_6N_2$ (326.4) | Calc | C 55.20 | H 6.80 | N 8.59 |
|---|---|---|---|---|
| | Found | C 54.92 | H 6.72 | N 8.36 |

(3) i=8.

1,8-octanediol bis(α-acetamido acrylate) Yield: 91%; $^1$H NMR (CDCl$_3$, 300 MHz): δ (ppm)=1.28 (m, 8H, CO$_2$CH$_2$CH$_2$C$\underline{H}_2$CH$_2$), 1.64(p, 4H, CO$_2$CH$_2$C$\underline{H}_2$), 2.05 (s, 6H, CH$_3$), 4.18 (t, 4H, CO$_2$C$\underline{H}_2$CH$_2$), 5.79 (s, 2H, vinyl C$\underline{H}$), 6.52 (s, 2H, vinyl C$\underline{H}$), 7.68 (s, 2H, N$\underline{H}$)

| $C_{18}H_{28}O_6N_2$ (368.4) | Calc | C 58.68 | H 7.66 | N 7.61 |
|---|---|---|---|---|
| | Found | C 58.46 | H 7.81 | N 7.47 |

Although the present invention has been described with reference to certain preferred embodiments thereof, other versions are readily apparent to those of ordinary skill in the art. Therefore, the spirit and scope of the appended claims should not be limited to the description of the preferred embodiments contained herein.

What is claimed is:
1. A multifunctional monomer for use as a cross-linking agent in polymer coatings having the formula

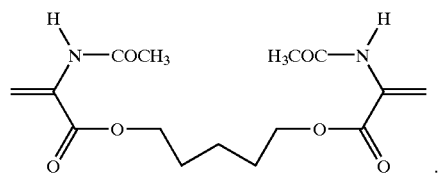

* * * * *